United States Patent [19]

Krupka et al.

[11] 4,413,224

[45] Nov. 1, 1983

[54] MICROPOWER SYSTEM

[76] Inventors: Yaakov Krupka, 8 Derech Yavne, Rehovot; Avi Bachar, 27 Cirelson St., Petah Tiqua; Shmuel Yerushalmi, 38 Hanassi Harishon St., Rehovot, all of Israel

[21] Appl. No.: 379,338

[22] Filed: May 18, 1982

Related U.S. Application Data

[63] Continuation-in-part of Ser. No. 145,245, Apr. 30, 1980, abandoned.

[30] Foreign Application Priority Data

Apr. 30, 1979 [IL] Israel .................................... 57186

[51] Int. Cl.$^3$ .............................................. G05F 1/46
[52] U.S. Cl. ................................... 323/222; 323/283; 323/284; 363/21; 363/97
[58] Field of Search .................... 323/222, 282–285; 363/18–21, 97, 124

[56] References Cited

U.S. PATENT DOCUMENTS

| | | | |
|---|---|---|---|
| 3,771,040 | 11/1973 | Fletcher et al. ....................... | 363/21 |
| 3,913,006 | 10/1975 | Fillmore ............................... | 323/222 |
| 3,974,439 | 8/1976 | Holland ................................ | 323/222 |
| 3,995,177 | 11/1976 | Sirocka et al. .................... | 323/283 X |
| 4,087,850 | 5/1978 | Kolzumi ............................... | 363/21 |
| 4,155,112 | 5/1979 | Miller et al. .......................... | 363/21 |
| 4,233,563 | 11/1980 | Schanbacher ....................... | 307/290 |

FOREIGN PATENT DOCUMENTS 242982 9/1969 U.S.S.R. .............................. 323/222

OTHER PUBLICATIONS

Armstrong, "Power Circuit Go Monolithic", Electronics, vol. 49, No. 9, p. 138, Apr. 29, 1976.
Chang et al., "Current Switch Logic Circuit", IBM Tech. Discl. Bulletin, vol. 13, No. 5, Oct. 1970, pp. 1101–1102.
Loucks, "Considerations in the Design of Switching Type Regulators", Solid State Design, Apr. 1963, pp. 30–34.
Loksh et al., "A Precision Low-Voltage Economical Switch-Type Volt. Stabilizer", Instrument & Experimental Techniques, (USSR), vol. 17., No. 2, Pt. 2, pp. 472–473, Sep. 1974.
R. J. Apfel, "Universal Switching Regulator Diversifies Power Subsystem Applications", Computer Design, vol. 17, No. 3, (Mar. '78), pp. 103–112.
B. Harvey, "A 500 KHZ Switching Inverter for 12 V Systems", Electron, No. 172, Apr. 10, 1979, p. 14.
Ruddy, "Constant-Voltage Switching Regulator", IBM Technical Disclosure Bulletin, vol. 14, No. 9, Feb. 1972, pp. 2784, 2785.
Delco Electronics Application Notes 42, "28 Volt. Flyback Sw. Regulator", G.M. Corp., Dec. 1968.

*Primary Examiner*—William M. Shoop
*Assistant Examiner*—Peter S. Wong
*Attorney, Agent, or Firm*—Fleit, Jacobson, Cohn & Price

[57] ABSTRACT

A micropower DC/DC conversion system providing a stabilized voltage output at a predetermined voltage higher than that of the energy source. The system is powered by one or more primary cells in parallel or by a suitable battery, and the system is of special use with systems requiring low power at stabilized voltage which is substantially independent of the energy source impedance and load variations.

According to the preferred embodiment of the system the output voltage stabilization is controlled by voltage detection circuit based on C-MOS inverters which allows extremely low power drain. The system is of special value for use with electronic implantable devices such as cardiac pacemakers.

2 Claims, 9 Drawing Figures

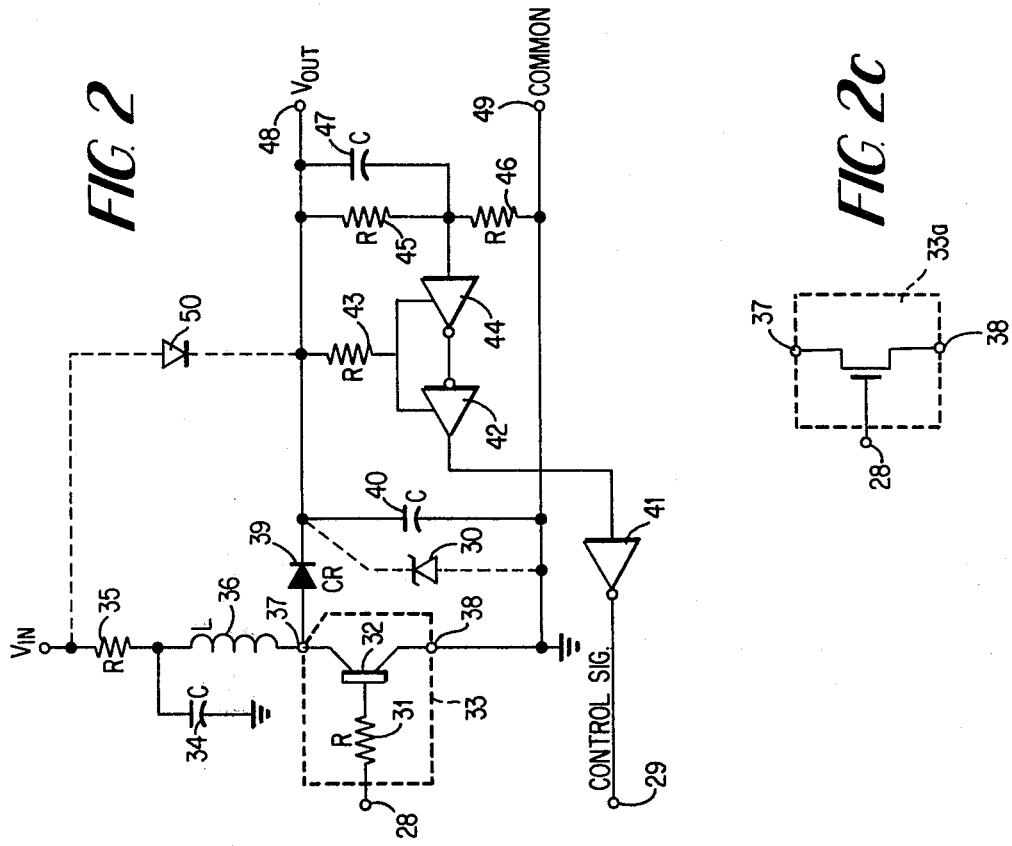
FIG. 2
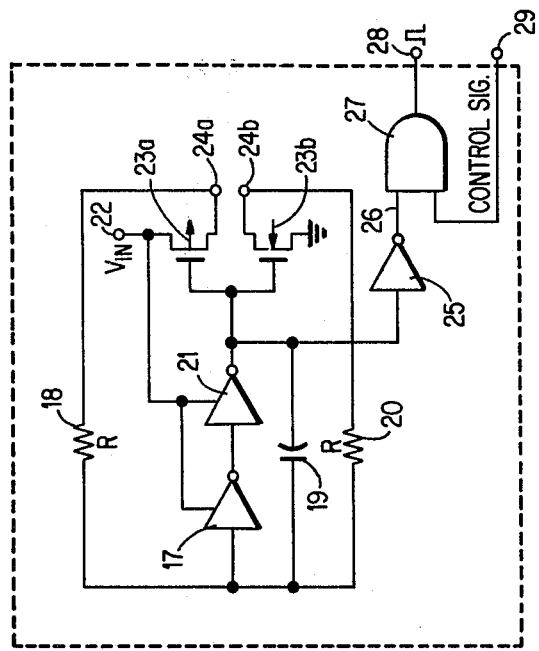
FIG. 2a
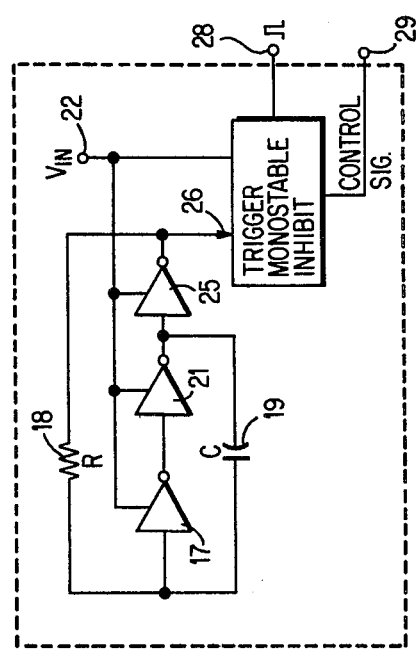
FIG. 2b
FIG. 2c

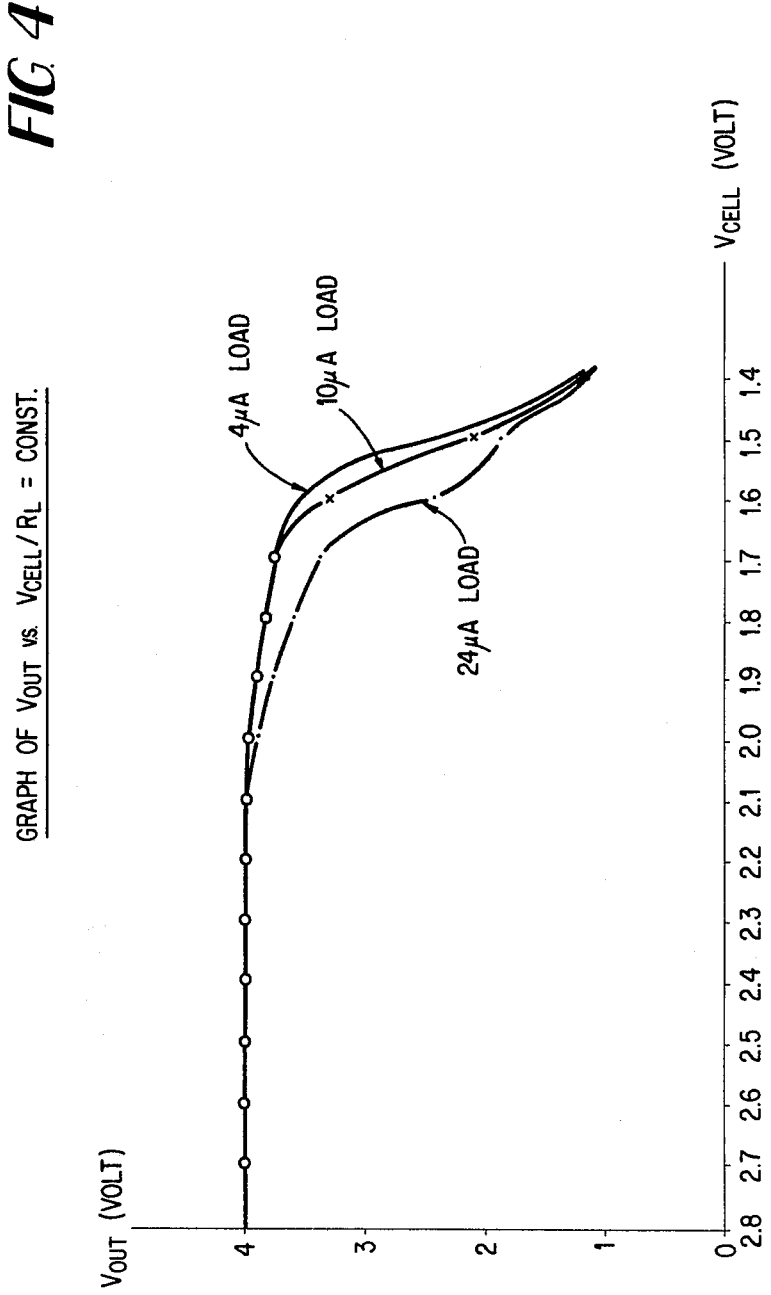

MICROPOWER SYSTEM

RELATION TO OTHER APPLICATIONS

The present application is a continuation-in-part of patent application Ser. No. 145,245 filed Apr. 30, 1980, now abandoned.

BACKGROUND OF THE INVENTION

Modern primary cells, such as lithium/iodine and lithium/chlorine cells are very efficient power sources for applications where a low output power is required. Amongst uses of such cells there may be mentioned their use as power source of medical devices such as tissue stimulating devices, and more particularly cardiac pacemakers of the implantable type. This type of cells is characterized by a very low internal leakage, chemical stability and excellent energy to volume ratio.

Amongst the drawbacks of this type of cells there may be mentioned the decrease of voltage and increase of internal impedance upon cell depletion and the relatively high specific gravity. Thus, it is desirable to use a single cell in order to decrease the overall weight of the device.

The output voltage of a single cell is too low for the intended purposes. For stimulating cardiac muscles a voltage of at least about 3.5 V is required in order to provide reliable stimulation. On the other hand the energy required is quite low, of the order of about 50 microjoules per pulse.

In order to be able to use such cells with this type of device, it is necessary to provide means for stepping up the voltage, supplied to the device. The output must be of predetermined elevated value, combined with high efficiency and stability versus cell voltage and load variations.

There exist various DC/DC conversion circuits for such applications. One of the more widely used ones is based on oscillator means combined with a low resistance starting current path. This type of device makes use of a high frequency oscillator which provides a comparatively high open circuit output voltage which is reduced by a serial type stabilizer resulting in substantial energy losses. Upon actuation a high current is drawn from the cell and there exists the danger of stoppage of oscillations in case of overload, resulting in possible cell depletion. In case of oscillator failure current supply to the device actuated is stopped and this is unacceptable with critical devices such as cardiac pacemakers.

Another conventional device comprising oscillator means, such as transformer coupled multivibrator has similar problems of voltage stabilization.

Switching type voltage multipliers are less efficient and as the output voltage is a multiple of the cell voltage, the output voltage varies according to the decrease of cell voltage upon cell depletion. Another disadvantage of the conventional DC/DC regulated systems is the use of zener diode as a voltage reference. Zener diode requires high current drain, of at least 50 $\mu$A, to allow reasonable voltage reference while for modern cardiac pacemaker the overall current drain is less than 20 $\mu$A including the output energy for heart stimulation.

SUMMARY OF THE INVENTION

The present invention relates to a micropower DC/DC conversion system providing a predetermined stabilized output voltage. The system overcomes the drawbacks of conventional systems.

According to the preferred embodiment of the system, a pair of C-MOS inverters with a common regenerative feedback resistor are used as a voltage detection circuit thus, high current reference devices such as zener diodes are ommitted, resulting in an extremely low current drain of the detection circuit of less than 1 $\mu$A.

The system can be actuated by a single primary cell and is adapted to provide a stabilized predetermined output voltage. The output voltage can be adjusted at will, and typically it is within the range of 3 V to about 20 V, depending on the intended use. Also higher voltages can be attained. Output voltage is quite stable, and the variations within a load of from zero to about 100 $\mu$A is less than about 2%. The efficiency of the system is over 70% when used with a high load and over 85% at loads in the 10 $\mu$A range.

Means are provided for applying the cell voltage directly to the load in case of system failure.

The combination of the above features makes possible the use of the novel device in critical life-saving medical devices such as cardiac pacemakers and the like.

BRIEF DESCRIPTION OF THE DRAWINGS

The invention is illustrated with reference to the enclosed schematical drawings, in which:

FIG. 2 illustrates part "a" of FIG. 1;

FIG. 2a illustrates pulse generating means and control gate for use in a device according to the invention;

FIG. 2b illustrates different pulse generating means with controlled monostable;

FIG. 2c illustrates a MOS-transistor used as switching device;

FIG. 4 is a graphical description of output voltage versus cell voltage under various load conditions.

DESCRIPTION OF THE PREFERRED EMBODIMENT

Figure 1:
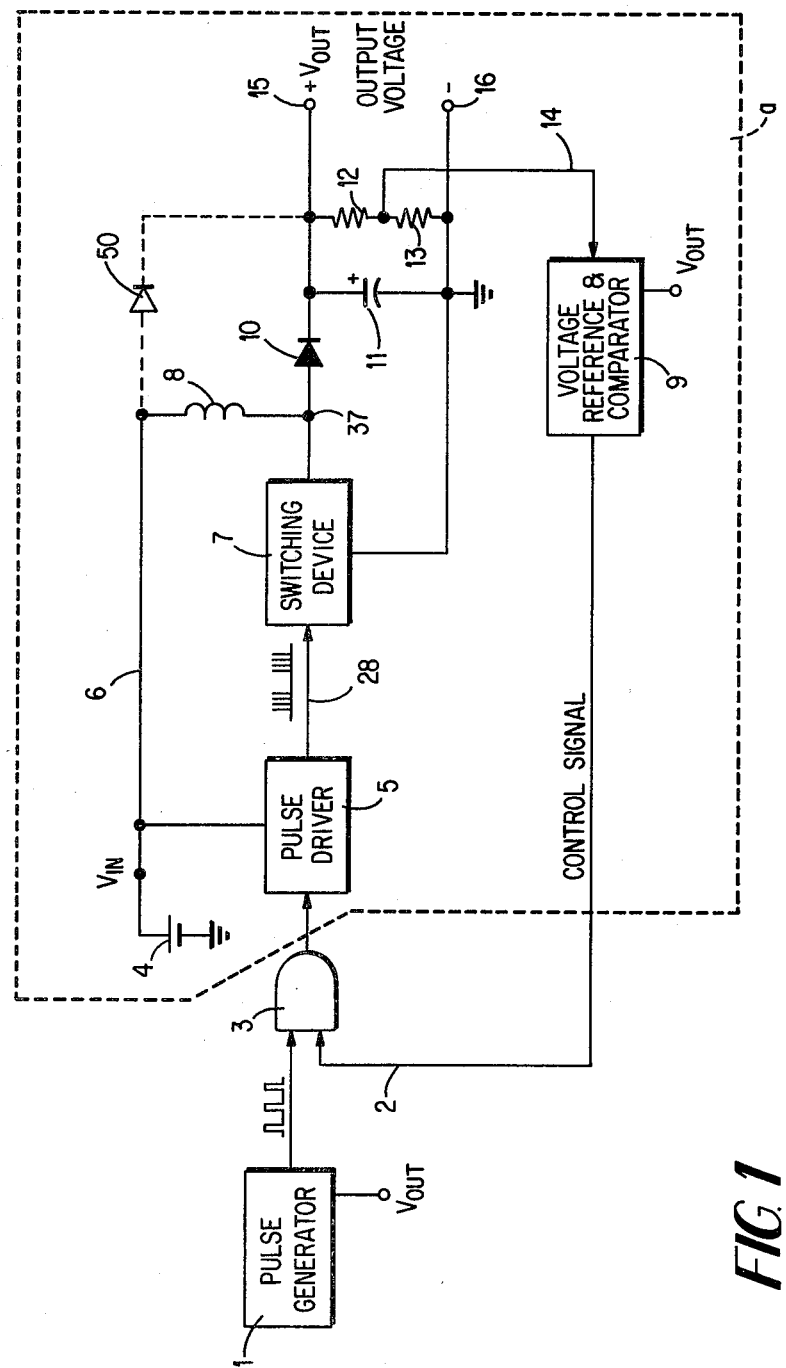
FIG. 1 is a partial block and partial circuit diagram of a device according to the invention.

As illustrated with reference to FIG. 1, the components of the DC/DC converter system of the present invention, which provides a stabilized voltage output, comprise in combination a power source 4, such as lithium primary cell, connected via pulse driver 5 and switching means 7, inductor 8, catch diode 10, an output capacitor 11 being in parallel with voltage divider resistors 12 and 13, and output voltage terminals 15 and 16. Further components of the system are the pulse generators means 1 and the pulse driver means 5.

The voltage conversion is effected by means of switching device 7, the inductor 8, the catch diode 10 and the output capacitor 11 and the energy source being the primary cell 4. Switching device 7 commutates inductor 8 first across energy source 4 for charge and after this in series with energy source 4, catch diode 10 and capacitor 11 for discharge. The charge-discharge sequence of the inductor 8 results in an energy transfer from the power source 4 to the capacitor 11. Thus, the output voltage at 15 increases as long as such commutation continues.

The main part of the loop is controlled by voltage detection circuit 9 and the AND-gate 3.

The voltage regulation is achieved by application of a sample of output voltage 14 to the voltage detection circuit 9, the output of which (generally being a digital output) is applied as signal 2 to AND-gate 3. A logic ZERO on the control signal 2 signifies that the voltage is of the predetermined voltage whereas a logic ONE means a drop of output voltage and thus a voltage value below the predetermined value. The AND-gate 3 passes driving pulses from pulse generator 1 as long as the control signal 2 is in logic ONE, i.e. as long as the output voltage is lower than desired. The pulses activate the switching device 7 via pulse driver means 5, resulting in a commutation of the inductor 8 for charge/discharge, resulting in an increase of the output voltage until the predetermined value is attained, changing the control signal 2 to logic ZERO, thus closing the regulation loop providing the desired voltage output at 15-16.

Figure 3:
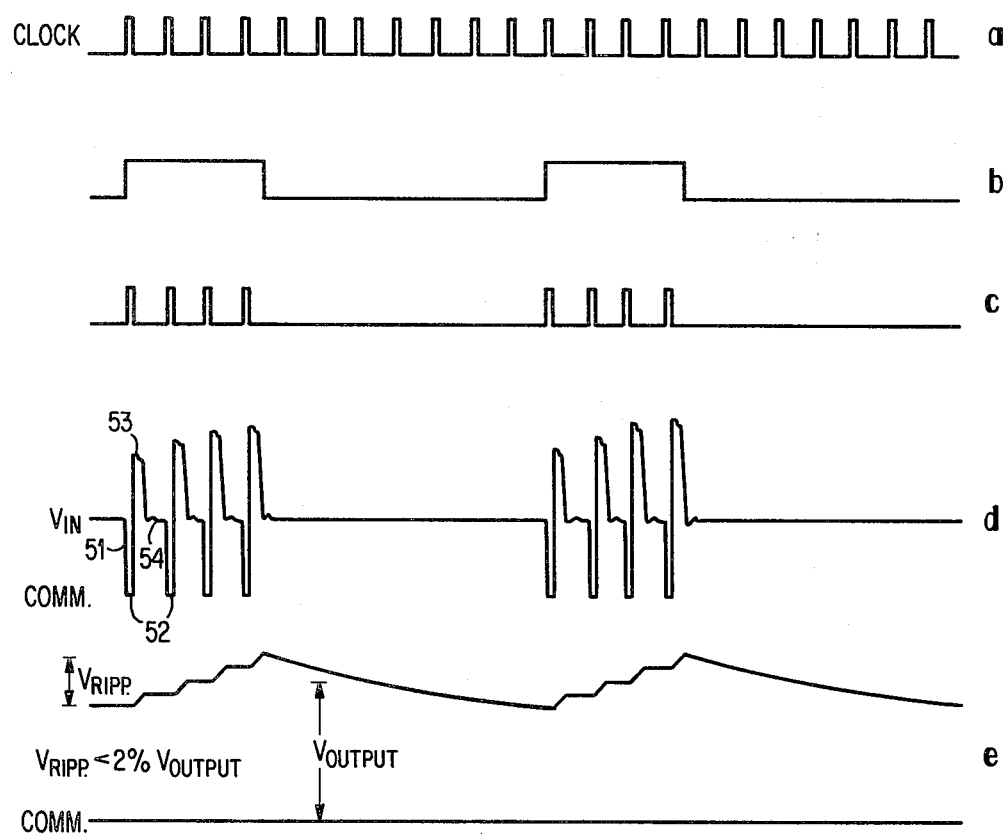
FIG. 3 illustrates waveforms associated with the novel DC/DC converter system.

FIG. 3 illustrates waveforms associated with the system. A typical pulse generator output waveform is shown as Clock (a). A typical waveform of control signal of FIG. 1 is shown as waveform (b). The resulting combined output waveform of the AND-gate 3 is shown as waveform (c). The waveform at the inductor 8, catch diode 10 and switching device 7 output junction is shown as waveform (d).

The switching means 7 connects inductor 8 to the common potential of the energy source 4 during the switching pulse period (52), and at the end of this switching period, the energy accumulated in inductor 8 maintains the current and thus the voltage increases abruptly to (53) where conduction of catch diode 10 occurs. This is indicated by the positive deflections to (53) on the waveform (d), transferring the energy stored in inductor 8 to capacitor 11, whereupon the voltage drops to (54), i.e. $V_{in}$.

A typical output waveform is shown as (e). The maximum ripple is generally within 2% of the predetermined output voltage.

FIG. 2 illustrates part "a" of FIG. 1.

According to one possible embodiment, shown in FIG. 2, the switching device 33 is a bipolar transistor with base limited current, resistor 31 being used as current limiting device. A current source incorporated within the pulse driving device such as C-MOS AND GATE 27 can be used to substitute resistor 31. The bipolar transistor 32 in 33 can be replaced by a suitable MOS-FET device as shown in FIG. 2c.

The C-MOS inverters 44 and 42 combine to act as a voltage detector for sensing the voltage from the divider 45, 46. Inverter 41 acts to buffer the output signal of inverter 42. Resistor 43 provides regenerative feedback for the voltage detector to allow negative slope of the inverter 44 threshold versus output voltage 48 as shown on FIG. 5a. The resistor 43 supplies regeneration feedback only during the transition periods and therefore eliminating current drain all other time. In addition, the resistor 43 acts as a current limiter during transition periods thus, decreasing further the current consumption of the voltage detector circuit. The output of 41 is characterized by a sharp rectangular wave for controlling the AND-gate 27 or monostable via line 29 shown in FIG. 2b. Capacitor 47 is used as a high pass filter of the output variations to the comparator input.

Zener diode 30 is an overvoltage protection device.

Figures 5, 5A:
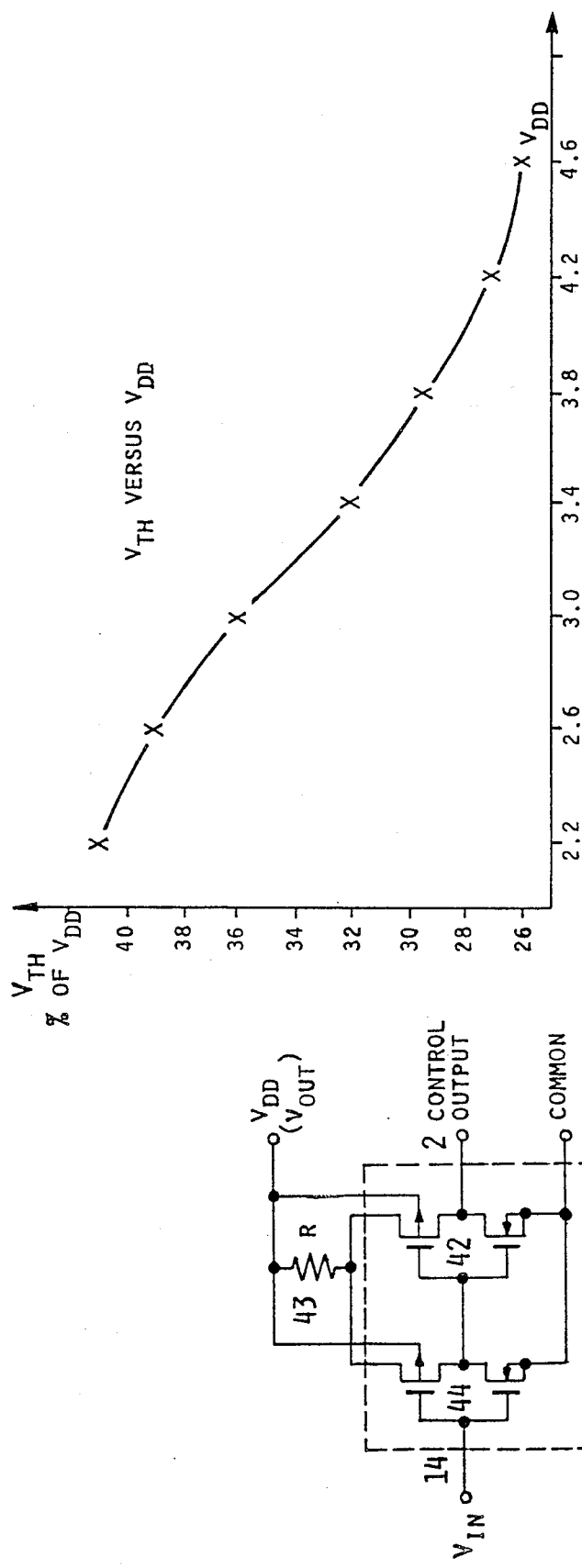
FIG. 5 is a detailed description of the C-MOS inverters with common resistor acting as voltage detection circuit.
FIG. 5a is graphical representation of the threshold voltage versus $V_{DD}$ for the voltage detection circuit of FIG. 5.

FIG. 5 is a detailed description of the voltage detector circuit comprised of C-MOS inverter devices such as 4007 drained by common resistor 43. FIG. 5a in a graphical representation of the threshold behaviour versus $V_{DD}$ which is an output voltage of the system.

A further embodiment of pulse generating circuitry is shown in FIG. 2a. A series of C-MOS inverters 17, and 21 are used for the oscillator circuitry. Resistors 18 and 20 with capacitor 19 comprise the time constant circuit for the oscillator. A combination of the resistors 18 and 20 establishes the duty cycle and the desired pulse width. Inverter 25 is used as a buffer between oscillator and driving gate 27.

FIG. 2b illustrates another pulse generator circuit. Here the oscillator generates square waveform and triggers a monostable circuit for generating sharp narrow pulses required for the switching device. It is clear that the same oscillator can be used in common with other parts of the powered system and therefore its current consumption could be subtracted from that of the conversion system in efficiency calculations.

FIG. 4 is a graphical representation of the output voltage versus energy source voltage at three representative load values. This graph was obtained from a prototype converter circuit, loaded by a pacemaker with energy supplied by a Lithium-Iodine cell. The pulse generator rate was dependent on cell voltage. Thus, decrease of 10% in rate occurred at 2 $V_{CELL}$. The output voltage fall indicates current limiting properties of the prototype converter.

According to a preferred embodiment there are used single primary cells having a voltage of more than 1 V and an internal impedance of less than about 100KΩ. Suitable cells are primary cells of the lithium/iodine or lithium chlorine type.

It is preferred that the pulse generator is an assymetrical multivibrator based on C-MOS devices. Yet a further pulse generator type is a C-MOS monostable multivibrator driven by C-MOS square wave multivibrator or by an external pulse generator providing pulses of predetermined duration and rate. The pulse generator is advantageously provided with means for adjusting the rate of pulses supplied as well as the pulse width so as to make possible telemetric measurements of the parameters of the energy source. The pulse driver is advantageously provided with means for controlling the length of pulse trains.

It is preferred to use a bipolar NPN or PNP high speed switching transistor or P-channel or N-channel high speed MOS-FET device as switching means.

The inductor used as energy transfer device is preferably wound on a soft ferrite core of toroid shape, or on a pot core, or use is made of an air coil, wherein the storage of energy is according to $$E = \frac{L \cdot i^2}{2}$$

where
  E is stored energy in Joules.
  L is inductance in Henrys
  i is maximum instantaneous current through the inductor, in Amperes.

The device is advantageously provided with a switching diode 39 of FIG. 2 which serves as a catch diode and which passes the current in case of absence of oscillations or when another fault occurs in the conversion system. The diode 39 is advantageously one with low leakage, low voltage drop and of high speed. The system is optionally provided with a diode 50 of the conventional type which allows passage of current from the energy source to the load when output voltage becomes lower than input voltage. The capacitor 40 can be of the electrolytic or dielectric type, with a very low leakage current. The voltage divider preferably comprises linear resistors of high resistance, and preferably of a resistance in the range of 10 to 50 MΩ.

It is clear that the above description is by way of illustration only and that various changes and modifications in the nature and arrangement of the components may be resorted to without departing from the scope and spirit of the use present invention.

We claim:

1. A DC/DC power conversion system including a power source for providing a stabilized voltage that is greater than a voltage provided by said power source, said conversion system employing a switching regulator and comprising:
   at least one primary electrochemical cell disposed in said power source;
   pulse generator means for providing a pulse train output;
   AND gate means for receiving a control input and responsive thereto for passing said pulse train output of said pulse generator means as a gate output;
   pulse driver means connected to said power source and to said AND gate means, and responsive to said gate output for providing a pulse driver output;
   MOS-FET switching means connected to said pulse driver means and responsive to said pulse driver output for issuing a commutation output;
   an inductor connected to said power source and to said MOS-FET switching means and responsive to said commutation output thereof for being commutated first across said power source to be charged and thereafter released providing a discharge output;
   a catch diode connected to said inductor for receiving said discharge output thereof, and issuing a diode output;
   an output capacitor connected to said catch diode for receiving and being charged by said diode output, and providing a capacitor output voltage which increases as long as said commutation of said inductor continues;
   a voltage-divider connected in parallel with said output capacitor for voltage-dividing to produce a divided output; and
   a voltage detector circuit comprising a pair of C-MOS inverters, drained via a common regenerative feedback resistor, the threshold of the C-MOS inverters serving as a voltage reference, said resistor also constituting current limiting means thereby resulting in an extremely low current drain of said inverters, said inverters being controlled by said divided output of said voltage-divider and issuing said control input to the said AND gate means.

2. The power conversion system of claim 1 wherein the power source comprises a primary cell having a voltage of at least 1 V and an internal impedance of up to 100KΩ.

* * * * *